(12) United States Patent
Bazin

(10) Patent No.: US 7,006,657 B2
(45) Date of Patent: Feb. 28, 2006

(54) METHODS FOR ENABLING EVALUATION OF TYPOLOGICAL CHARACTERISTICS OF EXTERNAL BODY PORTION, AND RELATED DEVICES

(75) Inventor: Roland Bazin, Bievres (FR)

(73) Assignee: L'Oreal S.A., Paris (FR)

( * ) Notice: Subject to any disclaimer, the term of this patent is extended or adjusted under 35 U.S.C. 154(b) by 695 days.

(21) Appl. No.: 10/024,034

(22) Filed: Dec. 21, 2001

(65) Prior Publication Data

US 2002/0090123 A1 Jul. 11, 2002

(30) Foreign Application Priority Data

Dec. 21, 2000 (FR) .................................. 00 16771

(51) Int. Cl.
*G06K 9/00* (2006.01)
(52) U.S. Cl. ...................................... 382/100; 434/377
(58) Field of Classification Search ............... 382/100, 382/108, 128; 348/77; 600/306; 434/377; 715/810, 835, 839; 705/26, 27
See application file for complete search history.

(56) References Cited

U.S. PATENT DOCUMENTS

| | | | |
|---|---|---|---|
| 3,571,947 A * | 3/1971 | Maddison et al. ............... | 35/17 |
| 4,276,570 A | 6/1981 | Burson et al. ............... | 358/903 |
| 4,670,781 A | 6/1987 | Aubert et al. .................. | 358/93 |
| 5,016,173 A | 5/1991 | Kenet et al. ........... | 364/413.13 |
| 5,796,862 A | 8/1998 | Pawlicki et al. ............. | 382/132 |
| 5,836,872 A | 11/1998 | Kenet et al. ................. | 600/306 |
| 6,719,565 B1 * | 4/2004 | Saita et al. .................... | 434/94 |
| 2003/0065589 A1 * | 4/2003 | Giacchetti ..................... | 705/27 |

FOREIGN PATENT DOCUMENTS

| | | |
|---|---|---|
| DE | 196 22 569 A1 | 12/1997 |
| EP | 1 030 267 A1 | 8/2000 |
| EP | 1 134 701 A2 | 9/2001 |
| FR | 2 565 481 A1 | 12/1985 |
| GB | 2 288 511 A | 10/1995 |
| JP | 3-11803 A | 5/1991 |
| JP | 5-253210 A | 10/1993 |
| JP | 7-289524 A | 11/1995 |
| JP | 10-21290 A | 1/1998 |
| JP | 11-185048 A | 7/1999 |
| JP | 2000-212038 A | 8/2000 |

(Continued)

OTHER PUBLICATIONS

Snead, K., "Bytes of Beauty: Selecting Makeup and Hair Color or Style has Moved into the Computer Age as the Industry Take Advantage of Technology," *Sun Sentinal,* Fort Lauderdale, Feb. 15, 1987, p. 3E.*

(Continued)

*Primary Examiner*—Andrew W. Johns
(74) *Attorney, Agent, or Firm*—Finnegan, Henderson, Farabow, Garrett & Dunner, L.L.P.

(57) ABSTRACT

A method of enabling evaluation of a typological characteristic of an external body portion of an individual comprises generating a sequence of images simulating varying degrees of at least one typological characteristic of an external body portion and enabling identification of at least one image within the sequence of images that substantially corresponds to a typological characteristic of the external body portion of the individual.

163 Claims, 6 Drawing Sheets

FOREIGN PATENT DOCUMENTS

| | | |
|---|---|---|
| JP | 2000-339331 A | 12/2000 |
| WO | WO 97/47235 A1 | 12/1997 |
| WO | WO 98/20458 A1 | 5/1998 |
| WO | WO 98/21695 A1 | 5/1998 |
| WO | WO 98/37811 A1 | 9/1998 |
| WO | WO 00/43956 A2 | 7/2000 |
| WO | WO 00/76398 A1 | 12/2000 |
| WO | WO 01/46906 A2 | 6/2001 |

OTHER PUBLICATIONS

Kravetz, S., "If That's Me in the E-Dressing Room, Why Doesn't This Fit?" *The New York Times,* Sep. 20, 2000, p. H22.*

English language Derwent Abstract of DE 196 22 569, Dec. 11, 1997.

English language Derwent Abstract of JP 5-253210, Oct. 5, 1993.

A.A. Bukharaev et al., "AFM investigation of selective etching mechanism of nanostructured silica," 19th European Conference on Surface Science, Madrid, Spain, vol. 485, pt. 2, Sep. 5-8, 2000, pp. 1319-1324.

Copy of Office Action dated Nov. 16, 2004, in copending Japanese Patent Application No. 2001-390564, (9 pages) and English Translation of Office Action (10 pages).

English language Derwent Abstract of JP 10-21290, Jan. 23, 1998.

English language Derwent Abstract of JP 11-185048, Sep. 7, 1999.

English language Derwent Abstract of JP 2000-212038, Aug. 2, 2000.

English language Derwent Abstract of JP2000-339331, Dec. 8, 2000.

English translation of JP H3-118036, published May 20, 1991.

English translation of JP H07-289524, published Nov. 7, 1995.

* cited by examiner

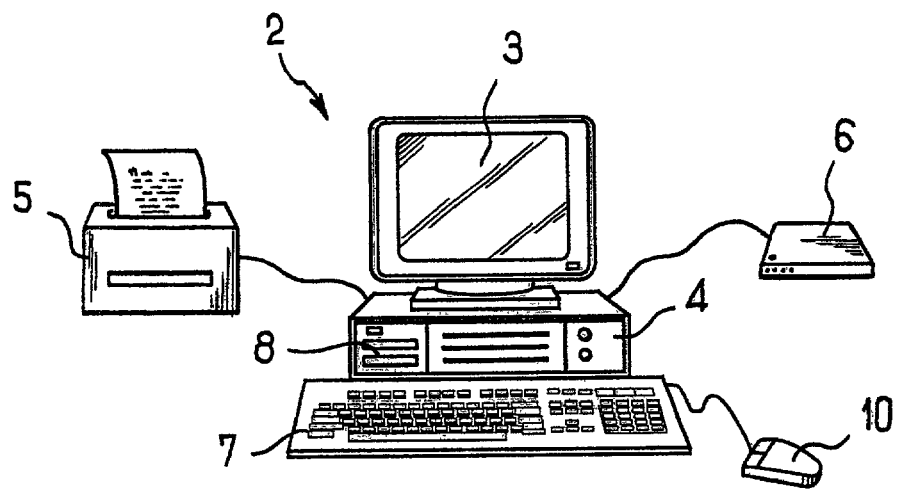
FIG_1
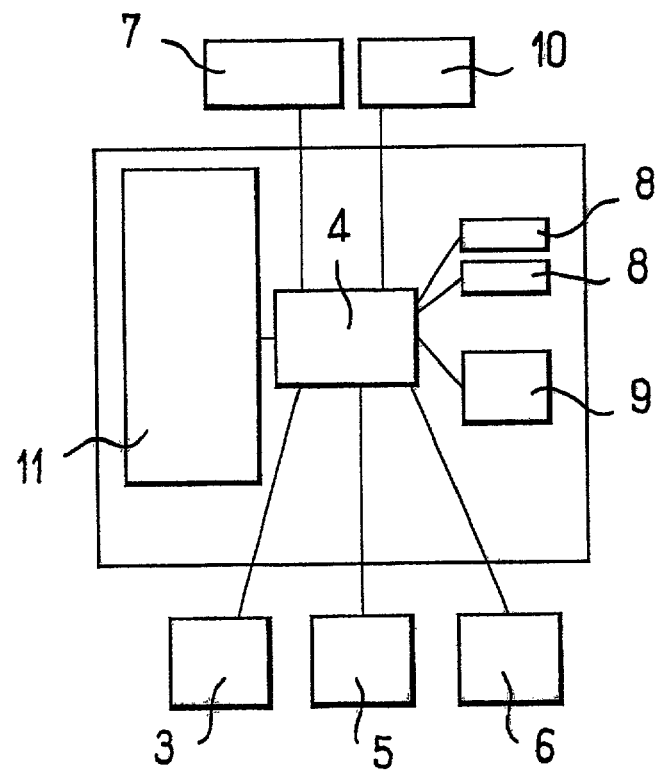
FIG_2

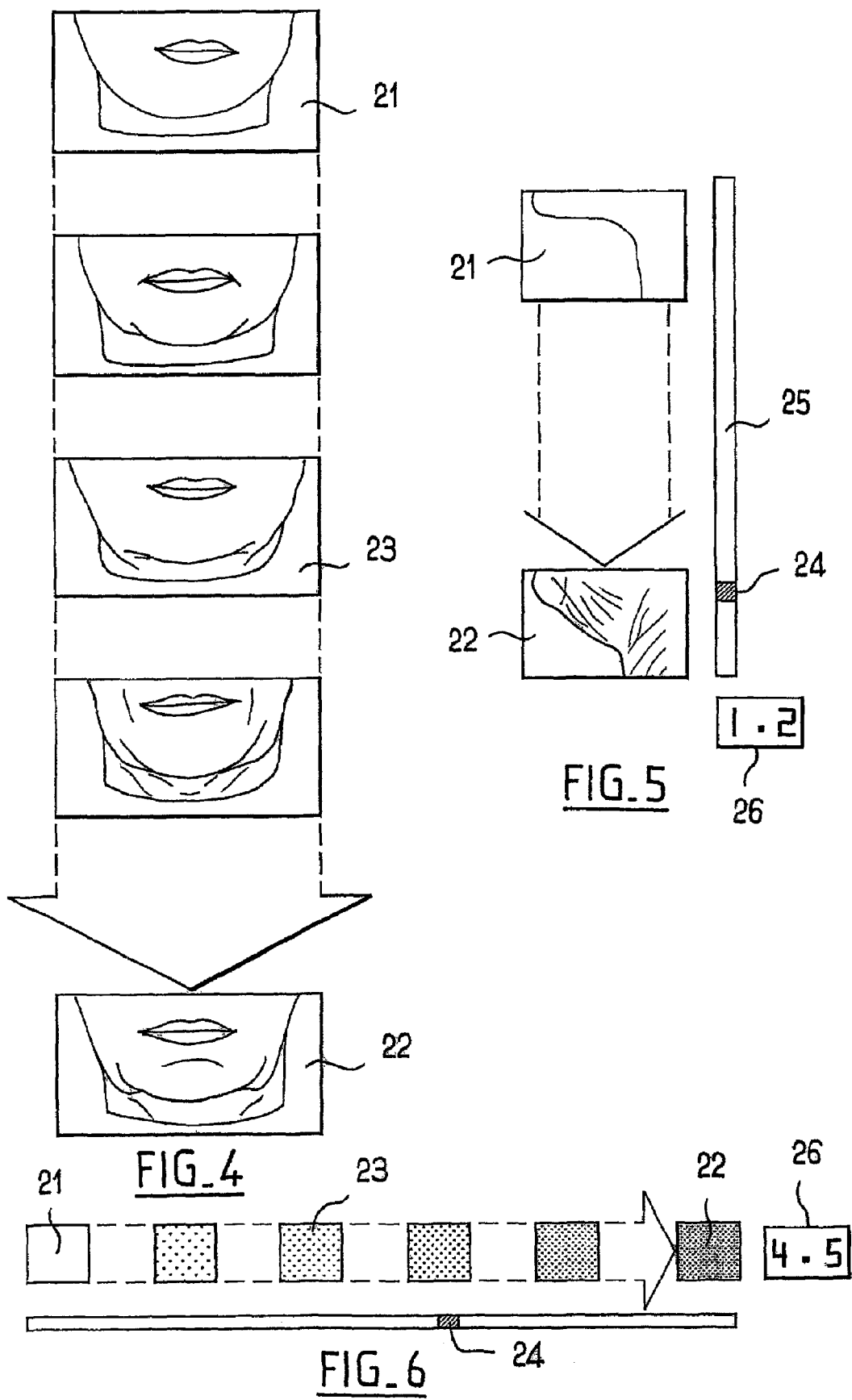

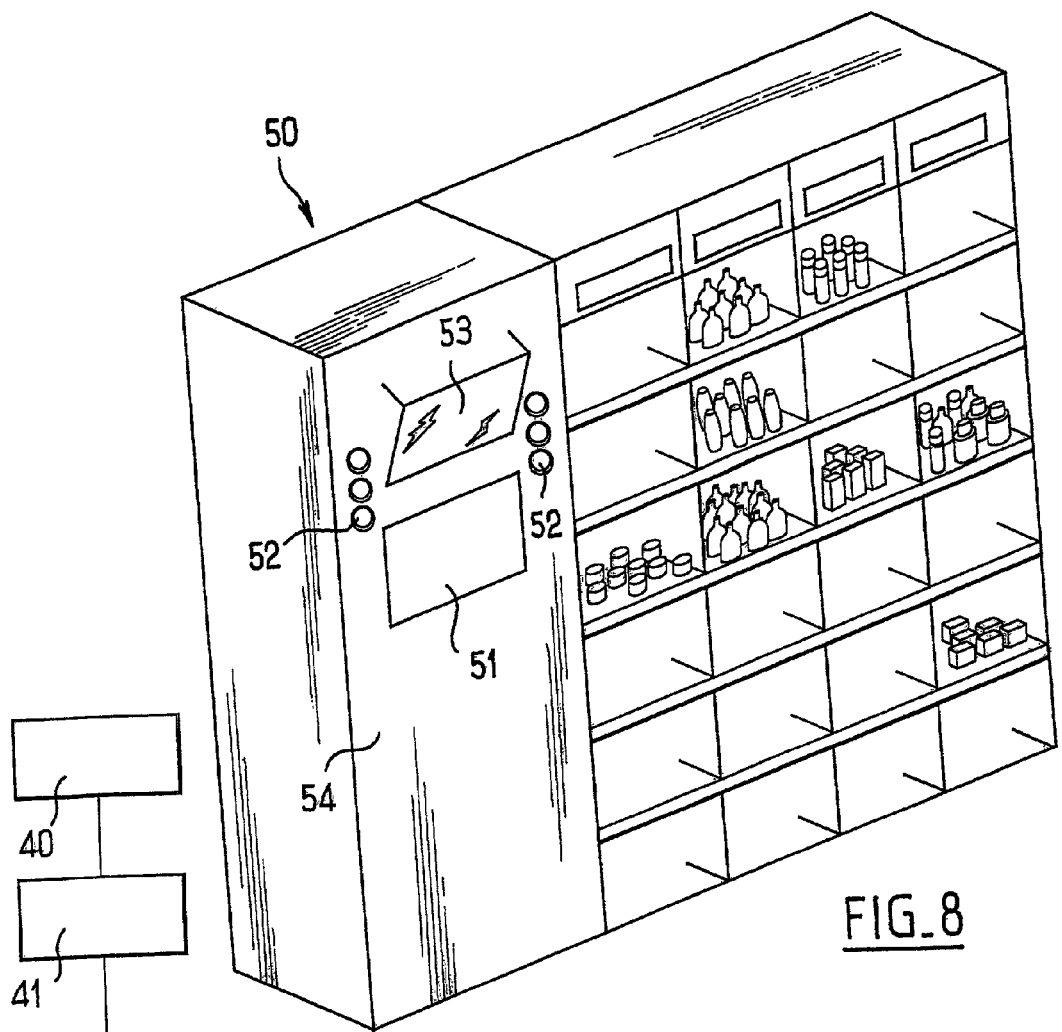
FIG.8
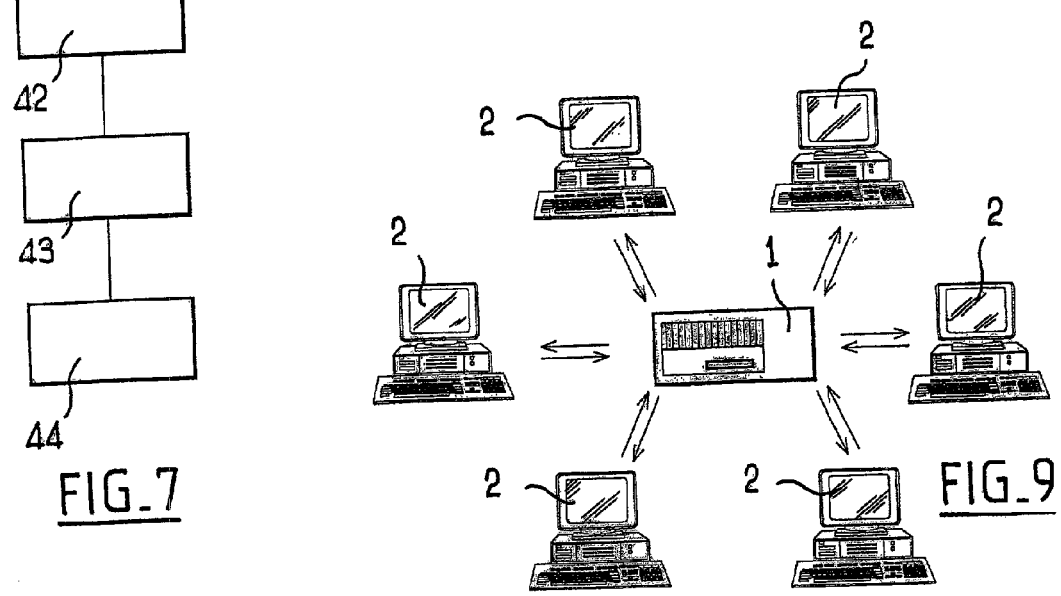
FIG.7
FIG.9

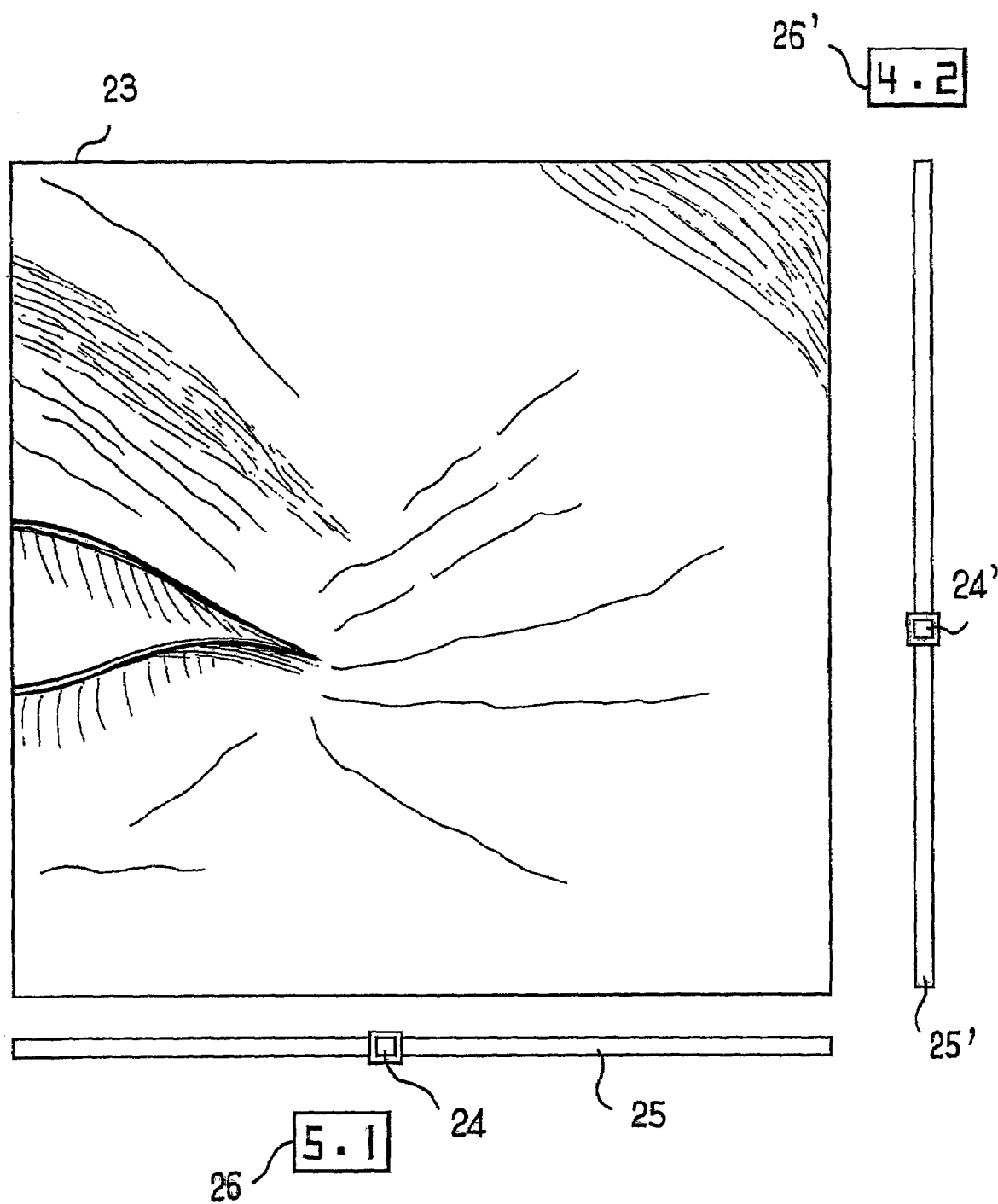
FIG_12

METHODS FOR ENABLING EVALUATION OF TYPOLOGICAL CHARACTERISTICS OF EXTERNAL BODY PORTION, AND RELATED DEVICES

The present invention relates to evaluating and/or analyzing typological characteristics of the body, for example, to establish a diagnosis.

Certain Internet sites recommend cosmetic and/or care products to Internet users on the basis of replies given by such users to questionnaires. For example, these sites may recommend products as a function of a user's age and/or on a reply given to a question relating to skin type, such as dry, normal, mixed, or greasy, for example. Other sites may ask for hair color, and assist the user in making a selection by displaying a color chart, or the like, of desired hair colors. Still other sites may ask the user to state the degree of wrinkles the user has, for example, very few, a few, or many wrinkles.

The various questionnaires available on these types of sites have questions that may be somewhat vague, which may make it difficult for a user to choose between several possible answers. This may lead to a relatively high degree of inaccuracy in the evaluation of various typological characteristics of the body of users.

The term "typological characteristic of the body" as used herein includes, for example, mechanical, morphological, or physiological characteristics, and also color characteristics such as complexion or hair color, for example.

British application GB 2 288 511 discloses a method for a remote diagnosis to be established. The method includes sending an image of a zone for diagnosis to a remote center where an expert can establish a diagnosis. Such a method typically requires the services of an expert and may not be suitable for self-evaluation. Further, the quality of the diagnosis may depend on the quality of the image sent to the expert, and thus on how well the picture was taken and on the lighting conditions, for example. This may make such a system relatively difficult to implement and not very reliable.

Currently, to relatively accurately evaluate typological characteristics of the body, such as slackening of the neck, firmness of the skin, cellulite, drooping eyelids, and/or wrinkles, for example, people typically visit an examination center where a professional such as a beautician examines the individual and performs the desired evaluation. This method may give rise to various costs associated with travel, reception, and remuneration of people who have had to travel to the examination center.

Furthermore, the people who are examined may not always be representative of the population as a whole, since they typically may be people who live close to an examination center. This may constitute a geographical barrier impeding objective evaluation.

To evaluate the state of the hair, for example, a known method includes cutting a lock of hair off and sending it to a diagnosis center where an expert can examine it. This method may not be very practical and diagnosis may take a relatively long time to establish, given the time it takes for the lock of hair to travel through the mail system.

It therefore may be desirable to evaluate a typological characteristic of the body accurately while reducing the cost of such evaluation.

Also, it may be desirable to establish a diagnosis relatively quickly, without assistance from a professional, and remotely if so desired.

Further, it may be desirable to enable a databank of various external body typologies to be built relatively easily and quickly.

Finally, it may be desirable to reveal early signs of improvement following cosmetic treatment, so as to encourage a person to persevere with a treatment, such as, for example, to determine the effectiveness of a cosmetic product and/or a care product.

The exemplary embodiments described herein may satisfy some or all of these needs. It should be understood that the invention could be practiced without performing one or more of the aspects described above. Other aspects will become apparent from the detailed description which follows.

As embodied and broadly described herein, the invention may include a method of enabling evaluation of a typological characteristic of an external body portion of an individual. The method may comprise generating a sequence of images simulating varying degrees of at least one typological characteristic of an external body portion and enabling identification of at least one image within the sequence of images that substantially corresponds to a typological characteristic of the external body portion of the individual.

The term "varying degrees" is used herein to mean that each image of the sequence has a different level or amount of the typological characteristic of interest. As an example, if the typological characteristic is number of wrinkles, the number of wrinkles may differ from one image to the next within the sequence, and thus the sequence contains images having varying degrees of wrinkles. In this manner, one image of the sequence may have very few wrinkles, the next image may have a few wrinkles, and the next image may have many wrinkles, for example. Or, if the typological characteristic is depth of wrinkles, the images in a sequence may span from an image having almost no wrinkles (i.e., a relatively smooth image) to an image having very deep wrinkles, with images in between these two extremes having differing depths of wrinkles from less deep to more deep. Further, if the typological characteristic is color, each image of the sequence may have different shade, for example from a lighter shade to a darker shade. Of course number of wrinkles and depth of wrinkles represent examples only and other degrees of typological characteristics will become apparent from the detailed description of the invention set forth herein.

"Enabling" an action may refer to one or more of a direct act of performing the action, and any indirect act of encouraging or being an accessory to the action. Thus, the terms include partnering or cooperating with an entity who performs the action and/or referring commerce to or having commerce referred from an entity who performs the action. Other examples of indirect activity encompassed within the definitions of "enabling" may include providing a subject with one or more tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling identification" or "enabling evaluation" do not necessarily require that the actor actually access or display anything. Rather, the actor may perform the enabling function by, for example, affiliating with an entity who performs the action, or by providing instructions, tools, or encouragement for another to do the accessing and displaying.

According to another aspect, a method of enabling evaluation of a typological characteristic of an external body portion of an individual may comprise generating a sequence of images simulating varying degrees of at least one typological characteristic of an external body portion, displaying the images of the sequence of images one at a time, and enabling identification of at least one image within the sequence of images that substantially corresponds to a typological characteristic of the external body portion desired by the individual.

The generating of the sequence may comprise generating images that simulate varying degrees of the at least one typological characteristic of the external body portion in at least a substantially continuous manner. The generating of the sequence of images may further comprise generating the sequence of images via a personal computer. The generating of the sequence of images also may comprise generating the sequence of images via a computer server. As an option, the generating of the sequence of images may comprise generating the sequence of images via an advice-giving apparatus. For example, the advice-giving apparatus may be provided at retail premises.

In certain embodiments, the method may further comprise displaying images of the sequence of images as an animated sequence. Or, the images may be displayed in response to an action of the individual. The action may comprise acting on a cursor of a scroll bar, clicking a button on a mouse, touching a monitor, depressing a key on a keyboard, moving an eye, or issuing a voice command, for example.

The method may further comprise displaying the images of the sequence of images on a monitor.

The method also may comprise gathering information associated with the at least one identified image. The information may be in the form of a number or an alphanumeric identifier, or some other similar type of information. The gathering of the information may be done at a location remote from the individual. For example, the individual may submit the identification and corresponding information over the Internet or via e-mail, for example, or the individual may send in the identification and corresponding information by mail.

The displaying of the images of the sequence of images may take place in a first geographical location and the information may be transferred to a second geographical location. The transferring of the information may comprise transferring the information via at least one communications protocol. The at least one communications protocol may comprises an Internet protocol, for example.

The method may further comprise storing and/or processing the transferred information. A diagnosis may be formed on the basis of the transferred information. Also, a database may be created of the transferred information.

The enabling of the identification may comprise enabling comparison of an image of the external body portion of the individual with at least one of the images of the sequence. The comparison may be done automatically by a computer or by the individual.

If done by a computer, the computer may compare an image of the external body portion of the individual with the images of the sequence of images. The image of the external body portion may be obtained by photographing or scanning, for example. The image of the external body portion of the individual also may comprise digital data that is compared with digital data representative of the images of the sequence.

The generating of the sequence of images may comprise generating the sequence of images via computation. The generating of the sequence of images may be done via morphing software. For example, at least one starting image and at least one end image may be provided, each of the starting image and the end image corresponding to differing degrees of the at least one typological characteristic of the external body portion. The morphing software may then create a series of intermediate images varying in the degree of typological characteristic between the starting image and the end image. The method may further comprise enabling a selection of the starting image and the end image from at least one image bank based on information relating to the external body portion of the individual to be evaluated.

The generating of the sequence of images may comprise generating the sequence of images based on information relating to the external body portion of the individual intended to be evaluated.

The sequence of images may comprise a plurality of sub-sequences. Each sub-sequence may be generated from a starting image and an end image. For example, the starting image of a sub-sequence of order n may correspond to the end image of the sub-sequence of order n−1.

The method also may comprise enabling modification of the at least one typological characteristic of the external body portion simulated by an image in response to movement of a cursor of a scroll bar. The at least one typological characteristic of the external body portion may comprise two typological characteristics and the enabling of the modification may be in response to movement of two cursors of two respective scroll bars.

Approximately 10 images, and/or 20 images, and/or 50 images may be generated in a sequence, or any other number of images that may be desirable to provide the varying degrees of the typological characteristic that individuals may have. The number of images also may be selected as a function of the desired accuracy for evaluating the typological characteristic.

Aside from morphing software, the generating of the sequence of images may be accomplished via graphics software and/or photographic film. The images may relate, for example, to a single subject wearing differing makeup from one picture to the next or to a single subject who has received a product that produces an effect on the typological characteristic in question of the body that varies over time, for example, a product for tensioning the skin to diminish wrinkles. These are only examples of course, and one could envision many other typological characteristics that could vary from one photograph to the next, either by taking photos of a single individual ore a plurality of individuals having differing degrees of at least one typological characteristic.

The enabling of the identification comprises enabling an individual to compare the at least one typological characteristic of the individual's external body portion with the at least one typological characteristic of the images of the sequence of images.

The generating of the images may comprise generating images simulating an appearance of a test device indicating the at least one typographical characteristic of an external body portion. As an example, the test device may be in the form of adhesive tape for picking up quantities of sebum.

Other test devices for analyzing topological characteristics of external body portions also may be utilized and are considered within the scope of the invention.

The generating of the images also may comprise generating images simulating an appearance of the external body portion.

Yet another aspect includes a method for enabling treatment of an external body portion of an individual. The method may comprise generating a sequence of images simulating varying degrees of at least one typological characteristic of an external body portion and enabling identification of at least one image within the sequence of images that substantially corresponds to a degree of the at least one typological characteristic of the external body portion of the individual. The method may further comprise determining a treatment for the external body portion of the individual based on the at least one identified image.

The method may also comprise enabling identification of at least one image within the sequence that substantially corresponds to a degree of the typological characteristic of the external body portion desired by the individual.

The determining of the treatment may comprise determining a treatment based on the degree of the at least one typological characteristic of the external body portion of the individual and the desired degree of the at least one typological characteristic.

Further, an order form for a product intended for the determined treatment of the external body portion may be transmitted, for example, via the Internet to the individual's computer or via the mail. The order form may list products intended for at least one of application to the external body portion and administration, for example, oral administration or the like, for treatment of the typological characteristic of the external body portion. The order form may list the product intended for the determined treatment.

The term treatment should be understood to encompass a wide variety of treatments, including, for example, a cosmetic treatment via make-up and the like, or a care treatment, via care products such as creams, lotions, vitamins, and other similar pharmaceuticals.

The method may further comprise sending to the individual the product, for example, either a sample of the product or the a regular-sized dosage of the product, intended for the determined treatment external body portion to the individual.

The method may further comprise enabling a comparison of the external body portion of the individual with the images of the sequence of images after the external body portion has been subjected to the determined treatment and enabling identification of which image of the sequence substantially corresponds to the typological characteristic of the treated external body portion of the individual. The method may further comprise recommending one of continuing the determined treatment and modifying the determined treatment based on the identification of the image substantially corresponding to the typological characteristic of the treated external body portion.

The determining of the treatment may comprise determining a product intended for treating the external body portion of the individual.

According to another aspect, a method of enabling evaluation of a treatment of an external body portion of an individual may comprise generating a sequence of images simulating varying degrees of at least one typological characteristic of an external body portion and enabling identification of at least one image within the sequence of images that substantially corresponds to a degree of the at least one typological characteristic of an external body portion of an individual so as to enable evaluation of the at least one typological characteristic prior to treatment. The enabling may occur before the external body portion of the individual is treated. The method may further comprise repeating the enabling of the identification and the evaluating after the external body portion has been treated and enabling a comparison of evaluations before the treatment and after the treatment.

Yet another aspect includes a method of generating a panel of potential users of a product. The method may comprise generating a sequence of images simulating varying degrees of at least one typological characteristic of an external body portion and for each individual in a group of individuals, enabling identification of at least one image within the sequence of images that substantially corresponds to a degree of at least one typological characteristic of an external body portion of each individual. The method may further comprise selecting amongst the individuals of the group those individuals whose identified images meet at least one predetermined criterion. For example, the predetermined criterion could include age, gender, a specific image identified or an identified image falling in a predetermined range of images of the sequence, or other similar criterion useful for grouping individuals to perform studies and the like.

The method may further comprise causing a treatment with a similar product of the external body portion of each of the individuals of the panel. An offer to purchase a product and/or a product for treating the external body portion may be provided to each individual of the panel.

In yet another aspect, a method of making a product intended to affect an external body portion of an individual may comprise generating a sequence of images simulating varying degrees of at least one typological characteristic of an external body portion and enabling identification of at least one image within the sequence of images that substantially corresponds to a degree of the at least one typological characteristic of the external body portion of at least one individual. The method also may comprise making a product based on the at least one identified image.

A panel of individuals may be formed by selecting from a group of individuals those individuals who identified at least one image that meets at least one predetermined criterion. The method may comprise causing one of an applying and an administering of the product that was made to each of the individuals of the panel.

After at least one of an application and an administration of the product, a comparison of the external body portion of each of the individuals on the panel with the images of the sequence of images and enabling identification of at least one image of the sequence of images that substantially corresponds to the at least one typological characteristic of the treated external body portion of each individual of the panel.

The method may further comprise enabling an evaluation of an
effectiveness of the product and modifying one of the product formulation and dosage, if necessary, based on the evaluation.

Yet another aspect includes a method of diagnosing comprising generating a sequence of images simulating varying degrees of at least one typological characteristic of an external body portion and enabling identification of at least one image within the sequence of images that substantially corresponds to a degree of said at least one typological characteristic of an external body portion of an individual to be diagnosed. The method may further comprise providing a diagnosis based on the at least one identified image.

The method also may comprise determining a treatment for the external body portion of the individual based on the diagnosis. The treatment may comprise one of administering a product to the individual and applying a product to the external body portion of the individual.

According to yet another aspect, a method of producing an atlas containing varying degrees of at least one typological characteristic of the body may comprise selecting at least one starting image corresponding to a degree of a typological characteristic of an external body portion and generating a sequence of images based on the starting image. The images of the sequence may substantially simulate varying degrees of the at least one typographical characteristic other than the degree associated with the at least one starting image. The method may further comprise selecting at least one image from the images of the sequence and providing the at least one selected image on a support so as to form an atlas comprising the at least one selected image. The generating of the sequence of images may comprise generating the sequence via image computation.

The image computation may be performed via one of graphics software and morphing software. For the latter, an end image also may be selected, the end image corresponding to a differing degree of the typological characteristic than the starting image. The sequence of images between the starting image and the end image may be generated, with the images of the sequence substantially simulating varying degrees of the at least one typographical characteristic between the degrees associated with the starting image and the end image.

The method may further comprise selecting a plurality of images of the sequence of images and providing each of the plurality of images on a respective support so as to form an atlas comprising the plurality of images. The support may be in the form of photographic paper or other similar paper product. Each image may be provided on a separate support and bound, or otherwise held together, to create the atlas.

According to this aspect, it may be possible to produce an atlas that is relatively accurate since the invention may substantially facilitate the generation of as many intermediate graduations as might be desired of a typological characteristic of the body. This may offer an improvement over atlases created by taking a series of pictures of individuals having differing degrees of a typological characteristic of an external body portion. Creating an atlas in this way may be time consuming and may require the various individuals to be compensated. Moreover, the number of differing degrees making up the atlas may be limited due to the limiting nature of having to photograph individuals having differing degrees of the typological characteristic.

Yet another aspect includes a method of generating a multi-vector database comprising generating at least one sequence of images simulating varying degrees of at least one typological characteristic of an external body portion. For each of a plurality of individuals, the method may further comprise enabling an identification of at least one image within the at least one sequence of images that substantially corresponds to the at least one typological characteristic of an external body portion of each individual. The method may also comprise creating a set of vectors, each vector corresponding respectively to an individual of the plurality of individuals and each vector comprising at least one component associated with information representative of the at least one identified image.

The method may further comprise generating at least two sequences of images, each sequence of images simulating differing typological characteristics. Each vector may comprise at least two components associated respectively with information representative of the at least two identified images from each of the at least two respective sequences of images.

Yet another aspect includes an apparatus for enabling evaluation of a typological characteristic of an external body portion of an individual. The apparatus may comprise a processor configured to perform any of the method described above.

The processor may be configured to generate images simulating varying degrees of the at least one typological characteristic in at least a substantially continuous manner.

The apparatus may further comprise a control mechanism enabling selection of an identified image. The control mechanism may be chosen from a button on a mouse, an action button displayed on one of a touch-sensitive monitor and a keyboard, a control by eye, and a control by voice, or other similar control mechanisms.

The apparatus also may comprise a data input mechanism and the generation of the images may be based on data input to the data input mechanism. The data input mechanism may be chosen from a keyboard and an action button displayed on a monitor, or any other data input mechanism used to input data into a computer or network or advice-giving apparatus. The data input into the data input mechanism may comprise a starting image and an end image selected from at least one image bank.

The apparatus may further comprise morphing software for generating the images of the sequence of images.

A monitor may be provided along with a generator configured to generate at least one scroll bar and at least one cursor enabling a scrolling of images of the sequence on the monitor, with only one image of a sequence of images being displayed at a time.

The generator may be configured to generate two scroll bars and two cursors.

The apparatus may also comprise a monitor for displaying the images of the sequence of images.

As an option, the apparatus may comprise a server and a transmission mechanism for transmitting to the server information representative of the at least one identified image.

Further, the apparatus may comprise a camera or a scanner, or some other similar mechanism for acquiring an image of the at least one typological characteristic of the external body portion of an individual.

A test device also may be provided for indicating the at least one typological characteristic of the external body portion of the individual being evaluated. The test device may be, for example, adhesive tape or the like.

The apparatus may comprise a validation mechanism for enabling the identified image to be validated.

As an option, the apparatus may comprise a monitor for displaying the images of the sequence and an indicator configured to be displayed on the monitor for indicating a degree of the at least one typological characteristic of the external body portion simulated by each image of the sequence.

The apparatus further may comprise a modem to enable communication with a server or a remote computer.

A computer system such as a neural network or some other artificial intelligence device also may be provided for comparing an image of an external body portion of an individual with the images of the sequence.

Yet another aspect of the invention includes a computer-readable medium containing instructions for performing any of the methods described above.

The term "providing" is used in a broad sense, and refers to, but is not limited to, making available for use, enabling usage, giving, supplying, obtaining, getting a hold of, acquiring, purchasing, selling, distributing, possessing, making ready for use, and/or placing in a position ready for use.

As used herein, the meaning of the term "images" includes any displayed or projected image, in either 2D or in 3D, or any non-displayed image, such as digital data stored in a memory or on a digital data recording medium, such as a hard disk or a CD-ROM.

The term "sequence" as used herein includes a series of images, wherein each image has a varying degree of at least one typological characteristic from one image to the next. The images of the sequence may correspond to differing degrees of the typological characteristics of the body that may vary continuously or substantially continuously. That is, an observer observing two successive images in the sequence may observe substantially no significant difference between them.

The sequence of images may be observed simultaneously or one at a time, or a subsequence of images within each sequence may be displayed at the same time, but at a different time than other subsequences of the sequence. The sequence of images also may be displayed as an animated sequence.

Each image may correspond to a representation of a region of the body, with or without makeup and with or without treatment. Alternatively, each image may correspond to the state of a test device, for example, an adhesive tape known under the trade name D'SQUAM.

The typological characteristics of the body may be selected, for example, from amongst the following:

characteristics relating to aging such as, for example, number and depth of wrinkles, slackening of the skin, which may occur in the neck region, for example, number and depth of creases, which may occur in the neck region, for example, skin creasing, depth of rings around the eyes, quantity of cellulite, drooping eyelids;

physiological and/or morphological characteristics such as number and size of skin flakes, quantity of sebum secretion, quantity of sweat secretion, dryness of the skin and/or the lips, length, curving, or density of the eyelashes and/or of the hair, irrigation of the skin by blood, lack of pigmentation, density of blackheads, spots of acne, blotchiness, moles, outline of the lips; and color of the skin and/or the hair.

Of course, this list is not intended to limiting, and those having skill in the art will recognize that a number of other typological characteristics of external body portions may be included within the scope of this invention.

Certain aspects may make it possible for a person to perform self-evaluation without the presence of a professional. Moreover, evaluation may also be independent of picture-taking conditions since, in an aspect, the method may be implemented without taking a picture of the person to be evaluated.

Some aspects of the invention also may permit the evaluation of typological characteristics of the body substantially without limiting the number of persons who can be evaluated. This is due to the vast number of users who may use the Internet or other network at the same time. As an example, it may be possible to set up a relatively large databank easily and quickly from a group comprising more than approximately 90 people, or, for example, more than approximately 1,000 people. Additionally, evaluation may be performed remotely, for example in the homes of the people being evaluated, which may eliminate any geographical barriers.

Since evaluation may take place in each person's home, it is possible to evaluate people who would not otherwise have been available to go to an examination center, such as people with relatively high purchasing power who may not be motivated by the kind of remuneration paid to people who attend examination centers for evaluation purposes, for example.

In certain embodiments, the information representative of the identified image may comprise a number, for example, a number in the form of a score, which may be proportional to the number of images between the selected image and one of the images corresponding to an extreme degree for the typological characteristic of the external body portion in question.

The images of the sequence of images need not necessarily be displayed on a screen, it may suffice to compare data in computer memory zones, for example.

Software other than morphing software also may be used for generating the sequence of images, such as, for example, graphics software for retouching images.

In an aspect, the sequence of images may be generated as a function of information about the person who is to be evaluated, for example numbers of wrinkles, skin type, age, sex, eye color, and other similar information. In this manner, the starting and end images from which the sequence of images is generated may be selected from at least one image bank as a function of information about the person to be evaluated.

As an option, each image of the sequence can be generated in real time. As an alternative, all of the images of the sequence can be generated in advance and stored prior to the step of selecting an image or a run of images from the sequence.

Besides the structural and procedural arrangements set forth above, the invention could include a number of other arrangements, such as those explained hereinafter. It is to be understood that both the foregoing description and the following description are exemplary. The accompanying drawings are included to provide a further understanding and are incorporated in and constitute a part of this specification. The drawings illustrate exemplary embodiments and, together with the description, serve to explain certain principles. In the drawings, FIG. 1 is a schematic view of an exemplary embodiment of a personal computer system;

FIG. 2 is a block diagram of various components of an exemplary embodiment of a personal computer system;

FIG. 4 is a schematic view of a sequence of images according to an exemplary embodiment of the invention;

FIG. 5 is a schematic view of extreme endpoints of a sequence of images according to an exemplary embodiment of the invention;

FIG. 6 is a schematic view of a sequence of images according to yet another exemplary embodiment of the invention;

FIG. 7 is a block diagram showing the steps of an exemplary method according to an aspect of the invention;

FIG. 8 is a perspective view of an exemplary embodiment of an apparatus for providing advice concerning cosmetics or care products;

FIG. 9 is a diagram representing an exemplary embodiment of a server connected to a plurality of personal computers;

Figure 11:
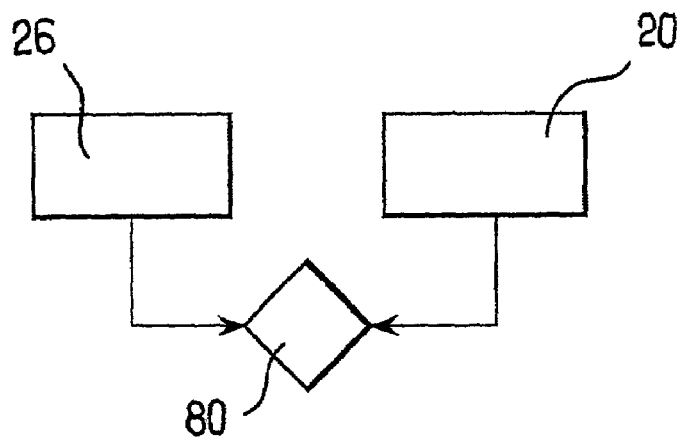

FIG. 11 is a schematic diagram showing steps for automatically determining a typological characteristic of the body according to an exemplary embodiment of the invention; and FIG. 12 is a schematic view of an image displayed on a screen together with two cursors associated with respective scroll bars, each cursor adapted to vary a degree of a typological characteristic of the body according to an exemplary embodiment of the invention.

Reference will now be made in detail to exemplary embodiments of the invention, examples of which are illustrated in the accompanying drawings. Wherever possible, the same reference numbers are used in the drawings and the description to refer to the same or like parts.

FIGS. 1 and 2 show an example of a personal computer system 2 comprising a central processing unit 4 connected to various external peripherals such as a monitor 3, a printer 5, a modem 6, a keyboard 7, a mouse 10, and to internal peripherals such as readers for CD-ROMS and floppy disks 8, and a hard disk 9. The central unit 4 may also be connected to working memory (RAM) 11.

Figure 3:
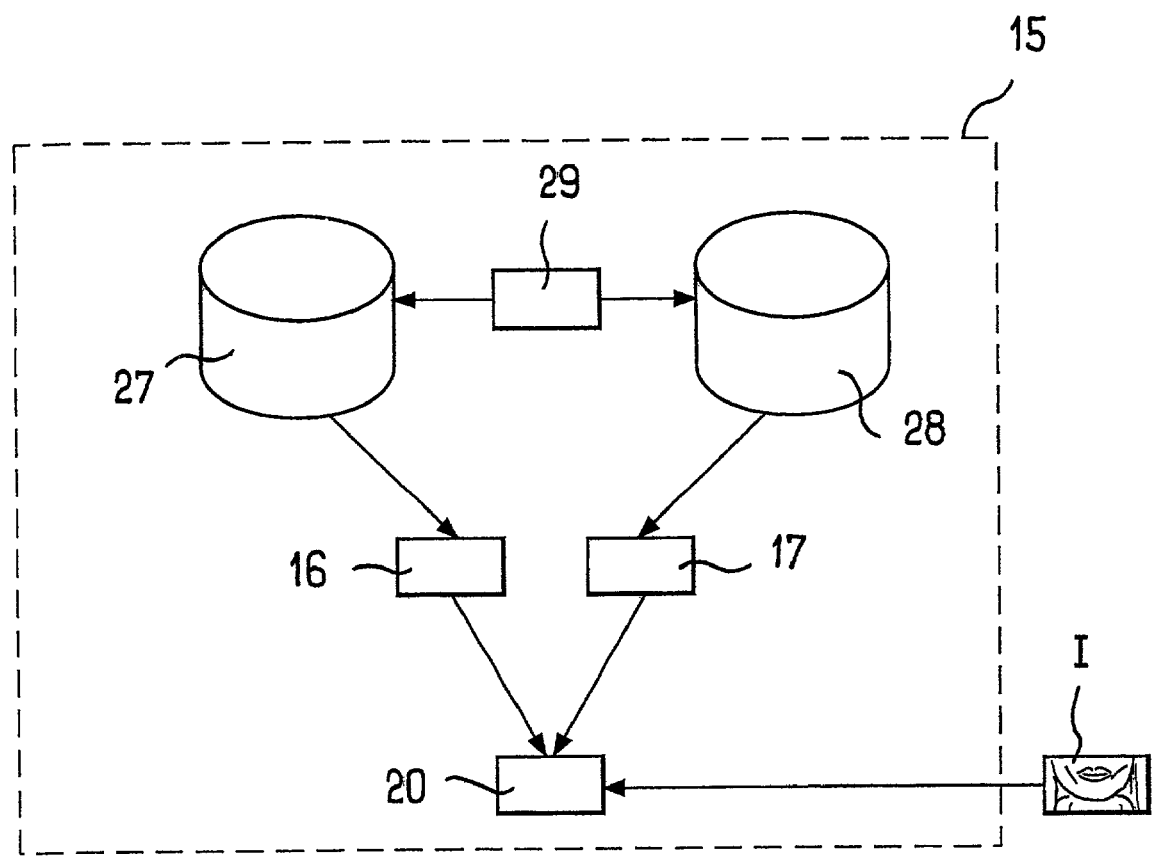
FIG. 3 is a block diagram showing various steps of an exemplary embodiment of the method according to an aspect of the invention.

In an exemplary embodiment of the invention, a program 15 represented diagrammatically in FIG. 3 is loaded into the personal computer 2. The program 15 may include morphing software 20 adapted to generate a sequence of intermediate images (or metamorphoses) between a starting image and an end image, which may be contained in respective files 16 and 17.

In the example described, the program 15 may cause a single image of the sequence to be displayed one at a time on the screen (i.e., monitor) 3.

FIG. 4 is a diagram showing an example of a sequence of images in which the firmness of the lower part of the face and the neck varies progressively from a starting image 21 to an end image 22. The sequence of images may pass through a series of intermediate images 23, with only a few of the intermediate images 23 being shown in FIG. 4. The intermediate images 23 show differing degrees of the firmness of the lower part of the face and the neck.

The invention is not limited to a particular typological characteristic of the body, and by way of example, FIG. 5 shows the starting and end images 21 and 22 for a sequence of images relating to slackening of skin on the neck. Other typological characteristics, including those discussed above, also may be displayed in the images, with the characteristics shown in FIGS. 4 and 5 serving as non-limiting examples only. Furthermore, external body portions other than the neck may be evaluated.

As an option, the various images of the sequence need not correspond to a representation of a portion of the human body, but can correspond to a representation of a test device, for example an adhesive tape, as shown in FIG. 6. As an example, FIG. 6 shows varying quantities of sebum which may be picked up by the tape.

The starting image 21 shows tape with no sebum deposited thereon, after being pressed against the skin and removed therefrom. The end image 22 shows the tape covered over a large fraction of its area by a deposit of sebum or other impurities.

Still further sequences of images can be generated, without thereby going beyond the ambit of the present invention, relating to other typological characteristics of the body.

The program 15 also may be arranged so as to cause a sequence of images to scroll image by image on the screen 3 while allowing an observer to stop on an image by pressing a key of the keyboard 7 or by clicking on a button of the mouse 10. Other control mechanisms also may be possible without thereby going beyond the ambit of the present invention, in particular use can be made of a touch-sensitive screen, voice commands, eye movements, and the like. The images 23 can also scroll as a function of action taken by an observer on a cursor 24 of a scroll bar 25, as shown in FIGS. 5 and 6.

The starting and end images 21 and 22 can be selected from a databank of respective starting and end images 27 and 28, as a function of information supplied to a selection engine 29, for example. Such an engine 9 can be used, for example, to display one or more questionnaires to a user and to process the corresponding replies from the user.

Before the various images 23 of a sequence are generated, the user can thus inform the program 15 about certain characteristics of the user's own body typology.

For example, with crow's foot wrinkles, the program 15 can prompt the user to specify the number of wrinkles present in the zone concerned by answering a questionnaire. A starting image having the number of wrinkles specified by the user may be selected from the starting image bank 27. An end image having the same number of wrinkles may also be selected from the end image bank 28. The computer may then display a crow's foot image having the number of wrinkles specified by the user.

In an exemplary embodiment, the typological characteristic of the body may be wrinkle depth, and the individual may act on the cursor of a scroll bar to modify the image gradually so as to increase or decrease wrinkle depth until the display image is an exact reflection of the user's own wrinkles.

The position of the cursor on the scroll bar then may provide wrinkle depth, and this position can be correlated, for example, with an alphanumeric information 26 being displayed on the screen. This information may then be transmitted where appropriate to a remote server for the purpose of drawing up a diagnosis and/or recommending a product that acts on wrinkles, for example.

The alphanumeric information 26 may be in the form of a score proportional to the number of images 23 in the sequence between the image displayed on the screen and the starting or end image. For example, an individual with young skin may achieve the highest score, for example 10/10, whereas an older person may have the lowest score, for example 0/10.

The various images 23 in a sequence may be generated in the examples described via, for example, morphing software 20. The morphing software 20 can be of any conventional type, for example computing pixel by pixel interpolations between two images, thereby enabling it to build up a continuous series of intermediate images 23 between the starting and end images 21 and 22.

Examples of morphing software include, but are not limited to, the programs known under the following names: WINMORPH V2.1; CINEMORPH 1.2; MPMORPH 4x; TSMORPH 32; FASTMORPHER 1.03; VISIONAIRE 1.0;

MORPH PLUS 1.04; V-MORPH 2.0; AGA MORPH 2.2, IMAGE MASTER 1.50R; ELASTIC DREAMS 1.01; and FANTASTIC DREAMS.

The program 15 can also have means for loading a file corresponding to an image of the external body portion of the person or the test device to be evaluated, as obtained using a scanner or a digital camera, for example.

The program 15 can also be arranged to cause the screen 3 to display simultaneously an image 23 from the sequence and the image of the external body portion of the person or the test device so as to make comparison easier.

The image of the person's external body portion or the test device can also be used in a comparison engine 80 of the artificial intelligence type as represented diagrammatically in FIG. 11, making it possible automatically to determine the degree of the typological characteristic of the body which corresponds to the person being evaluated.

The personal computer 2 can operate in self-contained manner, with the program 15 being loaded from a CD-ROM or a floppy disk, for example, or some other computer-readable medium.

Under such circumstances, the computer 2 may enable a user to perform self-evaluation by implementing the succession of steps illustrated in FIG. 7. In the first step 40, for example, the user of the personal computer 2 may reply to various questions and/or prompts enabling the program 15 to use the selection engine 29 to select a starting image 21 and an end image 22 from the banks of starting images and end images 28 and 29 respectively, for example, as a function of the age and the sex of the user, or other similar identifying descriptors.

Thus, if the person seeking to perform self-evaluation is a young woman, the starting and end images 21 and 22 will be different from those which may be selected if the user is an old man.

The following step 41 may comprise the morphing software 20 generating a sequence of images.

The next step 42 may correspond to identifying and then selecting an image of the sequence, either by stopping on the image by pressing a key of the keyboard or by positioning the cursor appropriately on the scroll bar, for example, or taking some other similar action. In certain embodiments, the individual may be prompted to make a selection of the identified image. The prompting may be either a direct prompt or an indirect prompt, such as remotely via a transmission over a network to the individual's personal computer or via software provided to the individual.

The following step 43 may be a step, for example, in which the program 15 creates a diagnosis as a function of the replies to the questionnaires and/or the prompts of the degree of the typological characteristic of the body as identified and subsequently selected.

The last step 44 can include, for example, recommending a product as a function of the diagnosis performed in the preceding step 43. As an example, such a product can be determined by searching through a database of cosmetics and/or care products for products having an action on the typological characteristic of the external body portion that has been evaluated and that are listed as being suitable for the profile (including the degree of the typological characteristic) of the person as evaluated. Alternatively, the user could supply the diagnosis to a professional, such as a beautician, either in person or remotely, and the professional could recommend a product based on the diagnosis.

The method of FIG. 7 may be implemented by means of a personal computer 2 as described above, with this computer being situated in the home of the person to be evaluated, for example. The diagnosis may be printed so that the user may subsequently supply it to a professional.

It would not go beyond the ambit of the present invention for evaluation to be performed on premises where cosmetic and care products are sold, for example as described with reference to FIG. 8.

FIG. 8 depicts an exemplary embodiment of an apparatus 50 for giving advice which may comprise a touch-sensitive screen 51 connected to a central processing unit (not shown), lighting devices 52, and a mirror 53. These devices may all be supported by a cabinet 54. By way of example, the cabinet 54 may stand next to shelves carrying various cosmetic and/or care products suitable for being recommended by the advice-giving apparatus 50 and for being identified by it.

Steps 40 to 44 in FIG. 7 can be performed using the advice-giving apparatus 50.

In an aspect of the invention, the personal computer 2 or advice-giving apparatus 50 may be connected to a server 1 as shown in FIG. 9, for example by means of the Internet.

By way of example, the server 1 can download the above-described program 15 to the personal computer 2. The user can thus download the program 15 from an Internet site, for example. Alternatively, software may be provided to the user via a CD-ROM or the like and sent via the mail or provided at a retail store.

The program 15 for generating the images 23 need not be downloaded, but may be used remotely. Under such circumstances, the personal computer 2 connected to the server 1 may act merely as a terminal.

When the program is consultable on-line, the Internet user may perform a self-evaluation or may be evaluated in the presence of a person trained for this purpose merely by connecting to the site that gives access to the program. Thus, the individual may obtain a diagnosis and, if appropriate, may have a cosmetic or care product recommended.

Furthermore, a manufacturer of cosmetic or care products can make use of the kind of data that such a site collects to obtain information potentially enabling the products it manufactures to be better adapted to the body typology of its client base.

Figure 10:
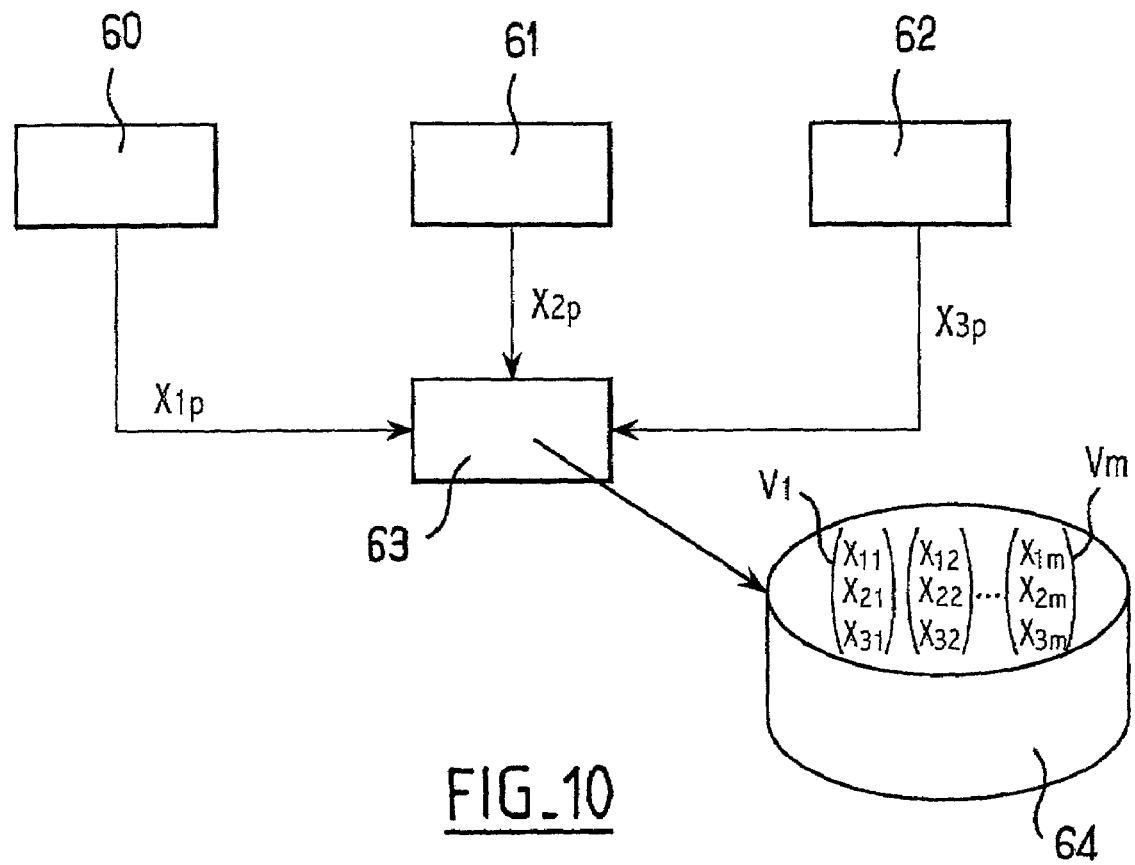
FIG. 10 is a diagram of steps for building a databank containing information relating to various typological characteristics of the body according to an exemplary embodiment of the invention.

In another exemplary aspect, the invention may be used to create a multi-vector databank bringing together data relating to a plurality of different typological characteristics of the body in a single person or alternatively of a group of people. FIG. 10 represents an exemplary embodiment of a composite image 63 that is the result of combining three images 60, 61, and 62 selected by a person performing self-evaluation or being evaluated, and relating respectively to typological characteristics of the body such as lower face typology, middle face typology, and upper face typology, for example.

By collecting together a set of composite images 63 or of data representative of such images, it is possible to build up a database in which each composite image 63 constitutes a kind of identikit portrait of the corresponding individual. The set of composite images 63 may be built up under identical conditions that are independent in particular of picture-taking conditions, thus possibly increasing the reliability of the data and facilitating comparisons.

It thus may be possible to build up a multi-vector databank 64 comprising a plurality of vectors $V_1, \ldots, V_n$ each having a component $X_{1q}, X_{2q}, X_{3q}$, where q is an integer in the range 1 to n, and n is the number of individuals who have served to build up the databank. Each component may be representative of an identified image in a sequence of images. For example, for individual number p in the group, identified image 60 can be associated with a numerical value $X_{1p}$, image 61 with a numerical value $X_{2p}$, and image 62 with a numerical value $X_{3p}$. Each vector $V_p$ may serve to quantify the body typology of individual number p in the group in a precise manner.

It also may be possible to evaluate a typological characteristic of the body relatively accurately, which may be advantageous for showing the effect of a cosmetic or care product on the typological characteristic of the body.

As an example, an evaluation may be performed prior to applying or administering a product and may again be performed after treatment of the external body portion. The results of the before and after evaluations may then be compared.

Given the relative accuracy made possible by certain embodiments of the invention, a change, such as an improvement, of the typological characteristic of the external body portion may be shown relatively quickly, which, if appropriate, may serve to encourage the person being treated to continue with the treatment.

In a similar manner, a person may be enabled to observe very quickly, by means of the invention, that some particular treatment is not effective and should therefore be changed or stopped.

The invention also may permit the monitoring of variation in a pathological condition, for example to decide whether treatment has become necessary.

The invention is not limited to the typological characteristics of the body mentioned above, and it can be applied to a large number of typological characteristics of the body, including sagging of the face, dryness of the skin, or evaluating the skin state of the neck, with this list not being limiting.

The above-described server 1 may also constitute an expert system of the artificial intelligence type arranged to give a diagnosis in completely automatic manner to an Internet user or other computer user who has conducted self-evaluation and has transmitted the results thereof to the server 1 or to a processor operating with a software program loaded thereon.

The invention is not limited to determining a single typological characteristic of the body at a time. By way of example, FIG. 12 shows an image 23 associated with two cursors 24 and 24' on respective scroll bars 25 and 25'. The cursors 24 and 24' serve respectively to modify wrinkle depth and wrinkle number. The numerical information 26 and 26' may represent the respective degrees of the corresponding typological characteristics of the body associated with each cursor 24, 24'. By moving the cursors 24 and 24', the user may change the number of wrinkles and/or the depth of the wrinkles.

The various examples described above can be applied to self-evaluation. Alternatively, evaluation also may be performed by a beauty consultant, on a stand for selling cosmetic or care products or in a beauty shop, for example, with the beauty consultant comparing the various images that appear on the screen with the person to be evaluated.

It may be possible to use other morphing software to generate the images in a sequence, and even cinematographic means and/or signal processing means, for example, for the purpose of acting on the contrast or the gray level or on certain colors of the image.

Depending on the position of a cursor, for example, it may be possible to decide to display one out of every x images in the sequence in order to potentially cause the modification of a typological characteristic of the body to be more marked and to take place more quickly when the cursor is moved, or in order to potentially facilitate an identification of two typological characteristics of the external body portion simultaneously.

A plurality of images representing various typological characteristics of the body can be displayed simultaneously on the screen, such as a lower face image and an upper face image, for example. Sequences also may comprise sub-sequences. A starting image of a sub-sequence of order n can be constituted by an end image of a sub-sequence of order n−1, the starting and/or end images of sub-sequences of order n and n−1 having at least typological characteristic of the body in common, and possibly more than one such characteristic.

Thus, in FIG. 12, the starting and end images of sub-sequences of order n and n−1 relating to wrinkle depth also may be used as starting or end images for sub-sequences relating to number of wrinkles.

It should be understood that the methods and devices discussed above are exemplary only and a variety of methods and devices relating to a sequence of images having a varying degree of a characteristic may be within the scope of the invention. In its broadest aspects, the present invention could be used to determine colors and textures for decorating and other similar characteristics that may be useful for evaluation, and particularly self-evaluation, purposes. Furthermore, the various structural components and materials are illustrative and exemplary only and one of ordinary skill in the art would recognize that other components enabling the performance of substantially the same functions may be used and are considered as within the scope of the invention.

It will be apparent to those skilled in the art that various modifications and variations can be made to the structure and methodology. Thus, it should be understood that the invention is not limited to the examples discussed in the specification. Rather, the present invention is intended to cover modifications and variations.

What is claimed is:

1. A method of enabling evaluation of a typological characteristic of an external body portion of an individual, the method comprising:
   generating a sequence of images simulating varying degrees of at least one typological characteristic of an external body portion; and
   enabling identification of at least one image within the sequence of images that substantially corresponds to a typological characteristic of the external body portion of the individual.

2. The method of claim 1, wherein the generating of the sequence comprises generating images that simulate varying degrees of the at least one typological characteristic of the external body portion in at least a substantially continuous manner.

3. The method of claim 1, wherein the generating of the sequence of images comprises generating the sequence of images via a personal computer.

4. The method of claim 1, wherein the generating of the sequence of images comprises generating the sequence of images via a computer server.

5. The method of claim 1, wherein the generating of the sequence of images comprises generating the sequence of images via an advice-giving apparatus.

6. The method of claim 5, further comprising providing the advice-giving apparatus at retail premises.

7. The method of claim 1, further comprising displaying images of the sequence of images as an animated sequence.

8. The method of claim 1, further comprising displaying the images of the sequence of images in response to an action of the individual.

9. The method of claim 8, wherein the action comprises one of acting on a cursor of a scroll bar, clicking a button on a mouse, touching a monitor, depressing a key on a keyboard, moving an eye, and issuing a voice command.

10. The method of claim 1, further comprising displaying the images of the sequence of images on a monitor.

11. The method of claim 1, further comprising gathering information associated with the at least one identified image.

12. The method of claim 11, wherein the information comprises a number.

13. The method of claim 11, wherein the gathering of the information comprises gathering the information at a location remote from the individual.

14. The method of claim 1, further comprising displaying images of a sequence of images in a first geographical location and transferring information representative of the identified image of the sequence of images to a second geographical location.

15. The method of claim 14, wherein the transferring of the information comprises transferring the information via at least one communications protocol.

16. The method of claim 15, wherein the at least one communications protocol comprises an Internet protocol.

17. The method of claim 14, further comprising at least one of storing and processing the transferred information.

18. The method of claim 17, further comprising forming a diagnosis based on the transferred information.

19. The method of claim 17, further comprising creating a database of the transferred information.

20. The method of claim 1, wherein the enabling the identification comprises enabling comparison of an image of the external body portion of the individual with at least one of the images of the sequence.

21. The method of claim 20, wherein the enabling the comparison comprises enabling a computer to perform the comparison.

22. The method of claim 20, wherein the image of the external body portion of the individual comprises a photographic image.

23. The method of claim 20, wherein the image of the external body portion of the individual comprises digital data.

24. The method of claim 1, wherein the generating of the sequence of images comprises generating the sequence of images via computation.

25. The method of claim 1, wherein the generating of the sequence of images comprises generating the sequence of images via morphing software.

26. The method of claim 25, wherein the generating of the sequence of images comprises providing at least one starting image and at least one end image, each of the starting image and the end image corresponding to differing degrees of the at least one typological characteristic of the external body portion.

27. The method of claim 26, further comprising enabling a selection of the starting image and the end image from at least one image bank based on information relating to the external body portion of the individual to be evaluated.

28. The method of claim 1, wherein the generating of the sequence of images comprises generating the sequence of images based on information relating to the external body portion of the individual intended to be evaluated.

29. The method of claim 1, wherein the sequence of images comprises a plurality of sub-sequences.

30. The method of claim 29, wherein each subsequence is generated from a starting image and an end image, the starting image of a sub-sequence of order n corresponding to the end image of the sub-sequence of order n−1.

31. The method of claim 1, further comprising enabling modification of the at least one typological characteristic of the external body portion simulated by an image in response to movement of a cursor or a scroll bar.

32. The method of claim 31, wherein the at least one typological characteristic of the external body portion comprises two typological characteristics, and wherein the enabling of the modification is in response to movement of two cursors of two respective scroll bars.

33. The method of claim 1, wherein generating the images of the sequence comprises generating at least approximately 10 images.

34. The method of claim 1, wherein generating the images of the sequence comprises generating at least approximately 20 images.

35. The method of claim 1, wherein generating the images of the sequence comprises generating at least approximately 50 images.

36. The method of claim 1, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

37. The method of claim 1, wherein the generating of the sequence of images comprises generating the sequence of images via one of morphing software, graphics software, and photographic film.

38. The method of claim 1, wherein the enabling of the identification comprises enabling an individual to compare the at least one typological characteristic of the individual's external body portion with the at least one typological characteristic of the images of the sequence of images.

39. The method of claim 21, further comprising producing the image of the typological characteristic of an external body portion of the individual via one of scanning and photographing.

40. The method of claim 1, wherein the generating of the images comprises generating images simulating an appearance of a test device indicating the at least one typographical characteristic of an external body portion.

41. The method of claim 40, wherein the test device comprises adhesive tape for picking up quantities of sebum.

42. The method of claim 1, wherein the generating of the images comprises generating images simulating an appearance of the external body portion.

43. An apparatus for enabling evaluation of a typological characteristic of an external body portion of an individual, the apparatus comprising:
a processor configured to perform the method of claim 1.

44. The apparatus of claim 43, wherein the processor is configured to generate images simulating varying degrees of the at least one typological characteristic in at least a substantially continuous manner.

45. The apparatus of claim 43, further comprising a control mechanism enabling selection of an identified image.

46. The apparatus of claim 45, wherein the control mechanism is chosen from a button on a mouse, an action button displayed on one of a touch-sensitive monitor and a keyboard, a control by eye, and a control by voice.

47. The apparatus of claim 43, further comprising a data input mechanism, wherein the generation of the images is based on data input to the data input mechanism.

48. The apparatus of claim 47, wherein the data input mechanism is chosen from a keyboard and an action button displayed on a monitor.

49. The apparatus of claim 47, wherein the data input into the data input mechanism comprises a starting image and an end image selected from at least one image bank.

50. The apparatus of claim 43, further comprising morphing software for generating the images of the sequence of images.

51. The apparatus of claim 43, further comprising a monitor and a generator configured to generate at least one scroll bar and at least one cursor enabling a scrolling of images of the sequence on the monitor, with only one image of a sequence of images being displayed at a time.

52. The apparatus of claim 51, wherein the generator is configured to generate two scroll bars and two cursors.

53. The apparatus of claim 43, further comprising a monitor for displaying the images of the sequence of images.

54. The apparatus of claim 43, further comprising a server and a transmission mechanism for transmitting to the server information representative of the at least one identified image.

55. The apparatus of claim 43, further comprising one of a camera and a scanner for acquiring an image of the at least one typological characteristic of the external body portion of an individual.

56. The apparatus of claim 43, further comprising a test device for indicating the at least one typological characteristic of the external body portion of the individual being evaluated.

57. The apparatus of claim 56, wherein the test device comprises adhesive tape.

58. The apparatus of claim 43, further comprising a validation mechanism for enabling the identified image to be validated.

59. The apparatus of claim 43, further comprising a monitor for displaying the images of the sequence and an indicator configured to be displayed on the monitor for indicating a degree of the at least one typological characteristic of the external body portion simulated by each image of the sequence.

60. A computer-readable medium containing instructions for performing the method of claim 1.

61. A method of enabling evaluation of a typological characteristic of an external body portion of an individual, the method comprising:
generating a sequence of images simulating varying degrees of at least one typological characteristic of an external body portion;
displaying the images of the sequence of images one at a time; and
enabling identification of at least one image within the sequence of images that substantially corresponds to a typological characteristic of the external body portion desired by the individual.

62. The method of claim 61, wherein the generating of the sequence of images comprises generating images that simulate varying degrees of the at least one typological characteristic of the external body portion in at least a substantially continuous manner.

63. The method of claim 61, wherein the generating of the sequence of images comprises generating the sequence of images via a personal computer.

64. The method of claim 61, wherein the generating of the sequence of images comprises generating the sequence of images via a computer server.

65. The method of claim 61, wherein the generating of the sequence of images comprises generating the sequence of images via an advice-giving apparatus.

66. The method of claim 65, further comprising providing the advice-giving apparatus at retail premises.

67. The method of claim 61, wherein the displaying of the images comprises displaying the images as an animated sequence.

68. The method of claim 61, wherein the displaying of the images comprises displaying the images in response to an action of the individual.

69. The method of claim 68, wherein the action comprises one of acting on a cursor of a scroll bar, clicking a button on a mouse, touching a monitor, depressing a key Ion a keyboard, moving an eye, and issuing a voice command.

70. The method of claim 61, wherein the displaying of the images comprises displaying the images on a monitor.

71. The method of claim 61, further comprising gathering Information associated with the at least one identified image.

72. The method of claim 71, wherein the information comprises a number.

73. The method of claim 71, wherein the gathering of the information comprises gathering the information at a location remote from the individual.

74. The method of claim 61, wherein the displaying of the images comprises displaying the images at a first geographical location and transferring information representative of the identified image of the sequence of images to a second geographical location.

75. The method of claim 74, wherein the transferring of the information comprises transferring the information via at least one communications protocol.

76. The method of claim 75, wherein the at least one communications protocol comprises an Internet protocol.

77. The method of claim 74, further comprising at least one of storing and processing the transferred information.

78. The method of claim 77, further comprising creating a database of the transferred information.

79. The method of claim 61, wherein the generating of the sequence of images comprises generating the sequence of images via image computation.

80. The method of claim 79, wherein the generating of the sequence of images comprises generating the sequence of images via morphing software.

81. The method of claim 80, wherein the generating of the sequence of images comprises providing at least one starting image and at least one end image, each of the starting image and the end image corresponding to differing degrees of the at least one typological characteristic of the external body portion.

82. The method of claim 61, further comprising enabling modification of the at least one typological characteristic of the external body portion simulated by an image in response to movement of a cursor or a scroll bar.

83. The method of claim 82, wherein the at least one typological characteristic of the external body portion comprises two typological characteristics, and wherein the enabling of the modification is in response to movement of two cursors of two respective scroll bars.

84. The method of claim 61, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

85. The method of claim 61, wherein the generating of the sequence of images comprises generating the sequence of images via one of morphing software, graphics software, and photographic film.

86. The method of claim 61, wherein the generating of the images comprises generating images simulating an appearance of the external body portion.

87. A method for enabling treatment of an external body portion of an individual, the method comprising:
  generating a sequence of images simulating varying degrees of at least one typological characteristic of an external body portion;
  enabling identification of at least one image within the sequence of images that substantially corresponds to a degree of the at least one typological characteristic of the external body portion of the individual; and
  determining a treatment for the external body portion of the individual based on the at least one identified image.

88. The method of claim 87, further comprising enabling identification of at least one image within the sequence that substantially corresponds to a degree of the typological characteristic of the external body portion desired by the individual.

89. The method of claim 88, wherein the determining of the treatment comprises determining a treatment based on the degree of the at least one typological characteristic of the external body portion of the individual and the desired degree of the at least one typological characteristic.

90. The method of claim 87, further comprising gathering information associated with the identified image.

91. The method of claim 90, wherein the gathering of the information comprises gathering the information at a location remote from the individual.

92. The method of 91, wherein the gathering of the information comprises gathering the information via the Internet.

93. The method of claim 87, further comprising transmitting an order form for a product intended for the determined treatment of the external body portion.

94. The method of claim 93, wherein the order form lists products intended for at least one of application and administration, and wherein the order form lists the product intended for the determined treatment.

95. The method of claim 87, further comprising sending a product intended for the determined treatment external body portion to the individual.

96. The method of claim 87, further comprising enabling a comparison of the external body portion of the individual with the images of the sequence of images after the external body portion has been subjected to the determined treatment and enabling identification of which image of the sequence substantially corresponds to the typological characteristic of the treated external body portion of the individual.

97. The method of claim 96, further comprising recommending one of continuing the determined treatment and modifying the determined treatment based on the identification of the image substantially corresponding to the typological characteristic of the treated external body portion.

98. The method of claim 87, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

99. The method of claim 87, wherein the generating of the sequence of images comprises generating the sequence of images via one of morphing software, graphics software, and photographic film.

100. The method of claim 87, wherein the enabling of the identification comprises enabling the individual to perform the identification.

101. The method of claim 87, wherein the enabling of the identification comprises enabling a computer to perform the identification.

102. The method of claim 101, wherein the enabling the computer to perform the identification comprises enabling the computer to compare an image of a typological characteristic of the treated external body portion of the individual with the images of the sequence of images.

103. The method of claim 102, wherein the image of the typological characteristic of the external body portion of the individual is produced via one of scanning and photographing.

104. The method of claim 87, wherein the determining of the treatment comprises determining a product intended for treating the external body portion of the individual.

105. The method of claim 104, wherein the product is chosen from one of a care product and a cosmetic product.

106. The method of claim 104, wherein the treatment comprises one of administration of the product to the individual and application of the product to the external body portion of the individual.

107. The method of claim 87, further comprising displaying the images of the sequence of images one at a time.

108. A method of enabling evaluation of a treatment of an external body portion of an individual, the method comprising:
  generating a sequence of images simulating varying degrees of at least one typological characteristic of an external body portion;
  enabling identification of at least one image within the sequence of images that substantially corresponds to a degree of the at least one typological characteristic of an external body portion of an individual so as to enable evaluation of the at least one typological characteristic prior to treatment, wherein the enabling occurs before the external body portion of the individual is treated;
  repeating the enabling of the identification and the evaluating after the external body portion has been treated; and
  enabling a comparison of evaluations before the treatment and after the treatment.

109. The method of claim 108, further comprising gathering information based on each evaluation.

110. The method of claim 109, wherein the gathering of the information comprises gathering the information at a location remote from the individual.

111. The method of claim 108, further comprising displaying the images of the sequence of images one at a time.

112. A method of generating a panel of potential users of a product, the method comprising:

generating a sequence of images simulating varying degrees of at least one typological characteristic of an external body portion;

for each individual in a group of individuals, enabling identification of at least one image within the sequence of images that substantially corresponds to a degree of at least one typological characteristic of an external body portion of each individual; and selecting amongst the individuals of the group those individuals whose identified images meet at least one predetermined criterion.

113. The method of claim 112, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

114. The method of claim 112, wherein the generating of the sequence of images comprises generating the sequence of images via one of morphing software, graphics software, and photographic film.

115. The method of claim 112, wherein the enabling of the identification comprises enabling each individual to perform the identification.

116. The method of claim 112, wherein the enabling of the identification comprises enabling a computer to perform the identification.

117. The method of claim 116, wherein the enabling of the computer to perform the identification comprises enabling the computer to compare an image of the typological characteristic of the external body portion of the individual with the images of the sequence of images.

118. The method of claim 117, wherein the image of the typological characteristic of the external body portion of each individual is produced via one of scanning and photographing.

119. The method of claim 112, further comprising causing a treatment with a similar product of the external body portion of each of the individuals of the panel.

120. The method of claim 119, wherein the product is chosen from one of a care product and a cosmetic product.

121. The method of claim 119, wherein the treatment comprises one of administering the product to the individual and applying the product to the external body portion of the individual.

122. The method of claim 112, further comprising providing one of an offer to purchase a product and a product for treating the external body portion to each individual of the panel.

123. The method of claim 112, further comprising displaying the images of the sequence of images one at a time.

124. A method of making a product intended to affect an external body portion of an individual, the method comprising:

generating a sequence of images simulating varying degrees of at least one typological characteristic of an external body portion;

enabling identification of at least one image within the sequence of images that substantially corresponds to a degree of the at least one typological characteristic of the external body portion of at least one individual; and making a product based on the at least one identified image.

125. The method of claim 124, further comprising gathering information based on the at least one identified image.

126. The method of claim 125, wherein the gathering the information comprises gathering the information remotely.

127. The method of claim 124, further comprising forming a panel of individuals by selecting from a group of individuals those individuals who identified at least one image that meets at least one predetermined criterion.

128. The method of claim 127, further comprising causing one of an applying and an administering of the product to each of the individuals of the panel.

129. The method of claim 128, further comprising, after at least one of an application and an administration of the product, enabling a comparison of the external body portion of each of the individuals on the panel with the images of the sequence of images and enabling identification of at least one image of the sequence of images that substantially corresponds to the at least one typological characteristic of the treated external body portion of each individual of the panel.

130. The method of claim 129, further comprising enabling an evaluation of an effectiveness of the product and modifying one of the product formulation and dosage based on the evaluation.

131. The method of claim 124, wherein the product is chosen from a cosmetic product and a care product.

132. The method of claim 124, wherein the product is intended to be one of applied to the external body portion of the individual and administered to the individual.

133. The method of claim 124, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

134. The method of claim 124, wherein the generating of the sequence of images comprises generating the sequence of images via one of morphing software, graphics software, and photographic film.

135. The method of claim 124, wherein the enabling of the identification of the images comprises enabling the at least one individual to perform the identification.

136. The method of claim 124, wherein the enabling of the identification of the images comprises enabling a computer to perform the identification.

137. The method of claim 136, wherein the enabling of the identification to be performed by a computer comprises enabling the computer to compare an image of the typological characteristic of the external body portion of the individual with the images of the sequence of images.

138. The method of claim 137, wherein the image of the typological characteristic of the external body portion of the at least one individual is produced via one of scanning and photographing.

139. The method of claim 124, further comprising displaying the images of the sequence of images one at a time 140. A method of diagnosing, comprising:

generating a sequence of images simulating varying degrees of at least one typological characteristic of an external body portion;

enabling identification of at least one image within the sequence of images that substantially corresponds to a degree of said at least one typological characteristic of an external body portion of an individual to be diagnosed; and providing a diagnosis based on the at least one identified image.

141. The method of claim 140, further comprising gathering information based on the at least one identified image.

142. The method of claim 141, wherein the gathering of the information comprises gathering the information at a remote location from the individual being diagnosed.

143. The method of claim 140, further comprising displaying the diagnosis on a monitor of a computer.

144. The method of claim 143, wherein the computer is connected to a computer server.

145. The method of claim 140, wherein providing the diagnosis comprises providing the diagnosis from a location remote from the individual being diagnosed.

146. The method of claim 140, wherein the at least one typological characteristic of the external body portion is chosen from number of wrinkles, depth of wrinkles, slackening of skin, number of creases, depth of creases, depth of rings around eyes, quantity of cellulite, droopiness of eyelids, number of skin flakes, size of skin flakes, quantity of sebum secretion, quantity of sweat secretion, dryness of skin, length of hair, curving of hair, density of hair, pigmentation, density of blackheads, spots of acne, blotchiness, moles, outline of lips, and color.

147. The method of claim 140, wherein the generating of the sequence of images comprises generating the sequence of images via one of morphing software, graphics software, and photographic film.

148. The method of claim 140, wherein the enabling of the identification comprises enabling the individual to perform the identification.

149. The method of claim 140, wherein the enabling of the identification comprises enabling a computer to perform the identification.

150. The method of claim 149, wherein the enabling the computer to perform the identification comprises enabling the computer to compare an image of the typological characteristic of the external body portion of the individual with the images of the sequence of images.

151. The method of claim 150, wherein the image of the at least one typological characteristic of the external body portion of the individual is produced via one of scanning and photographing.

152. The method of claim 140, further comprising determining a treatment for the external body portion of the individual based on the diagnosis.

153. The method of claim 152, wherein the treatment comprises one of administering a product to the individual and applying a product to the external body portion of the individual.

154. The method of claim 153, wherein the product is chosen from a cosmetic product and a care product.

155. The method of claim 140, further comprising displaying the images of the sequence of images one at a time.

156. A method of producing an atlas containing varying degrees of at least one typological characteristic of the body, the method comprising:

selecting a starting image corresponding to a degree of a typological characteristic of an external body portion;

generating a sequence of images based on the starting image, the images of the sequence substantially simulating varying degrees of the at least one typographical characteristic other than the degree associated with the starting image;

selecting at least one image from the images of the sequence; and providing the at least one selected image on a support so as to form an atlas comprising the at least one selected image, wherein the generating of the sequence of images comprises generating the sequence via image computation.

157. The method of claim 156, further comprising selecting a plurality of images of the sequence of images and providing each of the plurality of images on a respective support so as to form an atlas comprising the plurality of images.

158. The method of claim 156, wherein the generating of the sequence comprises generating images that simulate varying degrees of the at least one typological characteristic of the external body portion in at least a substantially continuous manner.

159. The method of claim 156, wherein the generating the sequence of images comprises generating the sequence via one of morphing software and graphics software.

160. The method of claim 156, further comprising selecting an end image corresponding to a degree of the typological characteristic that differs from the degree of the starting image, wherein the generating the sequence of images comprises generating images substantially simulating varying degrees of the at least one typographical characteristic between the degrees associated with the starting image and the end image.

161. The method of claim 160, wherein the generating of the sequence of images comprises generating the sequence of images via morphing software.

162. A method of generating a multi-vector database, comprising:

generating at least one sequence of images simulating varying degrees of at least one typological characteristic of an external body portion;

for each of a plurality of individuals, enabling an identification of at least one image within the at least one sequence of images that substantially corresponds to the at least one typological characteristic of an external body portion of each individual; and creating a set of vectors, each vector corresponding respectively to an individual of the plurality of individuals and each vector comprising at least one component associated with information representative of the at least one identified image.

163. The method of claim 162, further comprising generating at least two sequences of images, each sequence of images simulating differing typological characteristics, wherein each vector comprises at least two components associated respectively with information representative of the at least two identified images from each of the at least two respective sequences of images.

* * * * *

UNITED STATES PATENT AND TRADEMARK OFFICE
CERTIFICATE OF CORRECTION

PATENT NO. : 7,006,657 B2  
APPLICATION NO. : 10/024034  
DATED : February 28, 2006  
INVENTOR(S) : Roland Bazin Page 1 of 1

It is certified that error appears in the above-identified patent and that said Letters Patent is hereby corrected as shown below:

Title page, Item [54] and Column 1, line 1,
Title, "PORTION" should read -- PORTIONS --.

Column 18,
Line 1, "subsequence" should read -- sub-sequence --.
Line 48, "typographical" should read -- typological --.

Column 20,
Line 20, "Ion" should read -- on --.
Line 25, "Information" should read -- information --.

Column 21,
Line 43, "of 91," should read -- of claim 91, --.
Line 54, "treatment external" should read -- treatment of the external --.

Column 24,
Line 61, "time" should read -- time. --.

Column 26,
Lines 3 and 32, "typographical" should read -- typological --.

Signed and Sealed this

Eleventh Day of July, 2006

JON W. DUDAS
*Director of the United States Patent and Trademark Office*